United States Patent
Howes et al.

(10) Patent No.: US 8,076,272 B2
(45) Date of Patent: Dec. 13, 2011

(54) METHOD OF MAKING A SYNTHETIC ALKYLARYL SULFONATE

(75) Inventors: Andrew J. Howes, Berkeley, CA (US); Curtis Bay Campbell, Hercules, CA (US); Sophany Thach, Houston, TX (US)

(73) Assignee: Chevron Oronite Company LLC, San Ramon, CA (US)

( * ) Notice: Subject to any disclaimer, the term of this patent is extended or adjusted under 35 U.S.C. 154(b) by 0 days.

(21) Appl. No.: 12/622,220

(22) Filed: Nov. 19, 2009

(65) Prior Publication Data

US 2011/0118154 A1    May 19, 2011

(51) Int. Cl.
*C09K 8/584* (2006.01)
*E21B 43/16* (2006.01)
*B01F 17/00* (2006.01)

(52) U.S. Cl. ............... 507/259; 166/305.1; 166/372; 507/256; 507/935; 507/936; 507/937; 516/200

(58) Field of Classification Search ............. 507/259, 507/256, 935, 936, 937; 166/305.1, 372; 516/200
See application file for complete search history.

(56) References Cited

U.S. PATENT DOCUMENTS

| | | | |
|---|---|---|---|
| 3,953,538 | A | 4/1976 | Boney |
| 4,225,737 | A | 9/1980 | Mikulicz et al. |
| 4,503,277 | A | 3/1985 | Himes |
| 4,536,301 | A | 8/1985 | Malloy et al. |
| 4,816,185 | A | 3/1989 | Parker |
| 5,750,818 | A | 5/1998 | Mehlberg et al. |
| 6,054,419 | A | 4/2000 | Le Coent |
| 6,551,967 | B2 | 4/2003 | King et al. |
| 6,989,355 | B1 | 1/2006 | Campbell et al. |
| 2007/0282125 | A1 * | 12/2007 | Campbell et al. ............... 562/91 |
| 2009/0163669 | A1 * | 6/2009 | Sinquin et al. ................ 525/343 |

OTHER PUBLICATIONS

Rosemarie Szotak's, Handbook of Molecular Sieves, 1992, New York, Van Nostrand Reinhold.

* cited by examiner

*Primary Examiner* — Timothy J. Kugel
(74) *Attorney, Agent, or Firm* — Josetta I. Jones

(57) ABSTRACT

A process for preparing an alkylaryl sulfonate comprising (a) reacting at least one meta-xylene compound with olefin or a mixture of olefins having from about 10 to about 20 carbon atoms, in the presence of an acid catalyst, wherein the resulting product comprises no more than 40 weight percent of 1-alkyl-2,4 dimethylsubstituted aromatic compound and at least about 60 weight percent of 1-alkyl-3,5 dimethyl substituted aromatic compound; (b) sulfonating the product of (a); and (c) neutralizing the product of (b) with a source of alkali or alkaline earth metal or ammonia.

20 Claims, No Drawings

METHOD OF MAKING A SYNTHETIC ALKYLARYL SULFONATE

FIELD OF THE INVENTION

The present invention is directed to a method of making a synthetic alkylaryl sulfonate that is derived by sulfonating an alkylated aromatic compound by reacting an aromatic compound with a mixture of olefins selected from olefins having from about 10 to about 20 carbon atoms in the presence of a Lewis or Bronsted acid catalyst. The sulfonated alkylated aromatic compound may be used as an enhanced oil recovery alkylate. These sulfonates exhibit superior performance as enhanced oil recovery surfactants, especially in reservoirs that have a temperature of 125 degrees F. to 180 degrees F., 37 degree API, a brine salinity of 16 g/l and a brine total dissolved solids (TDS) of 17500 mg/l.

BACKGROUND OF THE INVENTION

It is well known to catalyze the alkylation of aromatics with a variety of Lewis or Bronsted acid catalysts. Typical commercial catalysts include phosphoric acid/kieselguhr, aluminum halides, boron trifluoride, antimony chloride, stannic chloride, zinc chloride, onium poly(hydrogen fluoride), and hydrogen fluoride. Alkylation with lower molecular weight olefins, such as propylene, can be carried out in the liquid or vapor phase. For alkylations with higher olefins, such as $C_{16+}$ olefins, the alkylations are done in the liquid phase, often in the presence of hydrogen fluoride. Alkylation of benzene with higher olefins may be difficult, and typically requires hydrogen fluoride treatment. Such a process is disclosed by Himes in U.S. Pat. No. 4,503,277, entitled "HF Regeneration in Aromatic Hydrocarbon Alkylation Process," which is hereby incorporated by reference for all purposes.

These alkylated aromatics are then further reacted to produce sulfonates (i.e., surfactants) that may be used in enhanced oil recovery from various oil-containing reservoirs. It has been discovered that not all surfactants work in all reservoirs the same. Some surfactants, based upon their molecular structure, give better oil recovery in reservoirs that have a reservoir temperature of at least 185 degrees F., a 36 degree API, a brine salinity of 2500 ppm and brine dissolved solids (TDS) or 3000 ppm.

DESCRIPTION OF THE RELATED ART

Mikulicz et al., U.S. Pat. No. 4,225,737, discloses a process for the alkylation of an aromatic hydrocarbon with an olefin-acting alkylating agent. The aromatic hydrocarbon is comingled with a first portion of said alkylating agent in a first alkylation reaction zone at alkylation reaction conditions in contact with a hydrofluoric acid catalyst.

Boney, U.S. Pat. No. 3,953,538 discloses an alkylation process in which a stream of an olefinic material is mixed with an acid stream and polymerized to cause formation of a polymeric diluent for the high strength acid which is initially charged to the alkylation process.

Mehlberg et al., U.S. Pat. No. 5,750,818 discloses a process for the liquid phase alkylation in an alkylation reactor of a hydrocarbon substrate with an olefinic alkylating agent in the presence of an acid alkylation catalyst at least one hydrocarbon having a lower boiling point than the hydrocarbon substrate and with a substantial stoichiometric excess of the hydrocarbon substrate over the alkylating agent to form a liquid product mixture.

King et al., U.S. Pat. No. 6,551,967 discloses a low overbased alkaline earth metal alkylaryl sulfonate having a Total Base Number of from about 2 to about 30, a dialkylate content of 0% to about 25% and a monoalkylate content of about 75% to about 90% or more, wherein the alkylaryl moiety is alkyltoluene or alkylbenzene in which the alkyl group is a $C_{15}$-$C_{21}$ branched chain alkyl group derived from a propylene oligomer are useful as lubricating oil additives.

LeCoent, U.S. Pat. No. 6,054,419 discloses a mixture of alkyl aryl sulfonates of superalkalinized alkaline earth metals comprising (a) 50 to 85% by weight of a mono alkyl phenyl sulfonate with a C14 to C40 linear chain wherein the molar proportion of phenyl sulfonate substituent in position 1 or position 2 is between 0 and 13% and 15 to 50% by weight of a heavy alkyl aryl sulfonate, wherein the aryl radical is phenyl or not, and the alkyl chains are either two linear alkyl chains with a total number of carbon atoms of 16 to 40, or one or a plurality of branched alkyl chains with on average a total number of carbon atoms of 15 to 48.

Malloy et al., U.S. Pat. No. 4,536,301 discloses a surfactant slug used to recover residual oil in subterranean reservoirs. The slug comprises a mixture of (1) from about 1 to about 10% of a sulfonate of a mixture of mono- and dialkyl-substituted aromatic hydrocarbon which has been obtained by the alkylation of an aromatic hydrocarbon with an olefinic hydrocarbon in the presence of a hydrogen fluoride catalyst; (2) a lower alkyl alcohol which possesses from about 3 to about 6 carbon atoms; and (3) a nonionic cosurfactant comprising an ethoxylated n-alcohol which possesses from about 12 to about 15 carbon atoms.

Campbell et al., U.S. Pat. No. 6,989,355 discloses an under-neutralized alkylxylene sulfonic acid composition for enhanced oil recovery processes. This invention is also directed to a method for enhancing the recovery of oil from a subterranean reservoir which method employs the underneutralized alkylxylene sulfonic acid compositions of the present invention. The under-neutralized alkylxylene sulfonic acid compositions are employed in an aqueous media. The method optionally employs suitable co-surfactants, such as alcohols, alcohol ethers, polyalkylene glycols, poly (oxyalkylene)glycols and/or poly(oxyalkylene)glycol ethers.

Parker, U.S. Pat. No. 4,816,185 discloses reaction products $C_9$-$C_{30}$ alkylbenzenes with styrene and sulfonated derivatives thereof and processes for preparing such products and derivatives. The sulfonate salts of reaction products are especially useful as detergents.

None of the prior art recognizes that the surfactant of the presently claimed invention may be employed in a reservoir having a temperature of from about 120 degrees F. to about 180 degrees F., more preferably, having a temperature of from about 140 degrees F. to about 170 degrees F., most preferably having a temperature of from about 150 degrees F. to about 160 degrees F., and even more preferred having a temperature of greater than 150 degrees F.

SUMMARY OF THE INVENTION

In its broadest embodiment, the present invention is directed to a process for preparing an alkylaryl sulfonate comprising (a) reacting at least one meta-xylene compound with olefin or a mixture of olefins having from about 10 to about 20 carbon atoms, in the presence of an acid catalyst, wherein the resulting product comprises no more than 40 weight percent of 1-alkyl-2,4 dimethylsubstituted aromatic compound and at least about 60 weight percent of 1-alkyl-3,5 dimethyl substituted aromatic compound; (b) sulfonating the product of (a); and (c) neutralizing the product of (b) with a source of alkali or alkaline earth metal or ammonia.

Accordingly, the present invention is also directed to an alkylaryl sulfonate compound prepared by (a) reacting at least one meta-xylene compound with olefin or a mixture of olefins having from about 10 to about 20 carbon atoms, in the presence of an acid catalyst, wherein the resulting product comprises no more than 40 weight percent of 1-alkyl-2,4 dimethylsubstituted aromatic compound and at least about 60 weight percent of 1-alkyl-3,5 dimethyl substituted aromatic compound;
(b) sulfonating the product of (a); and
(c) neutralizing the product of (b) with a source of alkali or alkaline earth metal or ammonia.

The present invention is also directed to a method of recovering crude oil from a subterranean hydrocarbon containing formation which comprises
(a) reacting at least one meta-xylene compound with an olefin or a mixture of olefins having from about 10 to about 20 carbon atoms, in the presence of an acid catalyst, wherein the resulting product comprises no more than 40 weight percent of 1-alkyl-2,4 dimethylsubstituted aromatic compound and at least about 60 weight percent of 1-alkyl-3,5 dimethyl substituted aromatic compound; (b) sulfonating the product of (a); (c) neutralizing the product of (b) with a source of alkali or alkaline earth metal or ammonia; and (d) displacing said solution into the formation to recover hydrocarbons from a production well.

DETAILED DESCRIPTION OF THE INVENTION

While the invention is susceptible to various modifications and alternative forms, specific embodiments thereof are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DEFINITIONS

Olefins—The term "olefins" refers to a class of unsaturated aliphatic hydrocarbons having one or more carbon-carbon double bonds, obtained by a number of processes. Those containing one double bond are called mono-alkenes, and those with two double bonds are called dienes, alkyldienes, or diolefins. Alpha olefins are particularly reactive because the double bond is between the first and second carbons. Examples are 1-octene and 1-octadecene, which are used as the starting point for medium-biodegradable surfactants. Linear and branched olefins are also included in the definition of olefins.

Linear Olefins—The term "linear olefins," which include normal alpha olefins and linear alpha olefins, refers to olefins which are straight chain, non-branched hydrocarbons with at least one carbon-carbon double bond present in the chain.

Branched Olefins—The term "branched olefins" refers to a class of olefins comprising one or more alkyl branches per linear straight chain containing the double bond, wherein the alkyl branch may be a methyl group or higher.

$C_{10}$-$C_{20}$ Normal Alpha Olefins—This term defines a fraction of normal alpha olefins wherein the carbon numbers below 10 have been removed by distillation or other fractionation methods.

In one preferred embodiment of the present invention is a process for preparing a synthetic alkylaryl sulfonate comprising (a) reacting at least one meta-xylene compound with an olefin or a mixture of olefins having from about 10 to about 20 carbon atoms, in the presence of an acid catalyst, wherein the resulting product comprises no more than 40 weight percent of 1-alkyl-2,4 dimethylsubstituted aromatic compound and at least about 60 weight percent of 1-alkyl-3,5 dimethyl substituted aromatic compound; (c) sulfonating the product of (b); and (d) neutralizing the product of (c) with a source of alkali or alkaline earth metal or ammonia.

Meta-Xylene Compound

The meta-xylene compound employed in the present invention is prepared by methods that are well known in the art.

Olefin or Mixture of Olefins

Sources of Olefins

The olefin or mixture of olefins employed in this invention may be a mixture of linear olefins, a mixture of isomerized linear olefins, a mixture of branched or partially branched linear olefins or mixtures of any of the foregoing.

The olefins may be derived from a variety of sources. Such sources include the normal alpha olefins, linear alpha olefins, isomerized linear alpha olefins, dimerized and oligomerized olefins, and olefins derived from olefin metathesis. Another source from which the olefins may be derived is through cracking of petroleum or Fischer-Tropsch wax. The Fischer-Tropsch wax may be hydrotreated prior to cracking. Other commercial sources include olefins derived from paraffin dehydrogenation and oligomerization of ethylene and other olefins, methanol-to-olefin processes (methanol cracker) and the like.

The olefins may also be substituted with other functional groups, such as carboxylic acid groups, heteroatoms, and the like, provided that such groups do not react with the strong acid catalyst.

The olefin or mixture of olefins is selected from olefins with carbon numbers ranging from about 10 carbon atoms to about 20 carbon atoms. Preferably, the mixture of olefins is selected from olefins with carbon numbers ranging from about 12 to about 18 carbon atoms. In one embodiment from about 12 to about 14 carbon atoms were employed. In one embodiment from about 16 to about 18 carbon atoms were employed.

In another embodiment, preferably, the olefin or mixture of olefins is a mixture of olefins derived from linear alpha olefins or isomerized linear olefins containing from about 10 to about 20 carbon atoms. More preferably, the olefin or mixture of olefins is a mixture derived from linear alpha olefins or isomerized linear olefins containing from about 12 to about 18 carbon atoms. In one embodiment, the olefin or mixture of olefins is a mixture of olefins derived from linear alpha olefins or isomerized linear olefins containing from about 12 to about 14 carbon atoms. In one embodiment, the olefin or mixture of olefins derived from linear alpha olefins or isomerized linear olefins is a mixture of olefins derived from linear alpha olefins or isomerized linear olefins containing from about 16 to 18 carbon atoms.

In one embodiment, the mixture of olefins is a mixture of branched olefins. The mixture of branched olefins is preferably selected from polyolefins which may be derived from $C_3$ or higher monoolefins (i.e., polypropylene, polybutylenes or co-oligomers etc.). Preferably, the mixture of branched olefins is either polypropylene or polybutylenes or mixtures thereof.

Normal Alpha Olefins

Preferably, the mixture of linear olefins that may be used for the alkylation reaction is a mixture of normal alpha olefins selected from olefins having from about 10 to about 20 carbon atoms per molecule. More preferably the normal alpha olefin mixture is selected from olefins having from about 12 to about 18 carbon atoms per molecule. In one embodiment, the normal alpha olefin mixture is selected from olefins having from about 12 to about 14 carbon atoms per molecule. In one embodiment, the normal alpha olefin mixture is selected from olefins having from about 16 to about 18 carbon atoms per molecule.

In one embodiment of the present invention, the normal alpha olefins are isomerized using at least one of two types of acidic catalysts, solid or liquid. A solid catalyst preferably has at least one metal oxide and an average pore size of less than 5.5 angstroms. More preferably, the solid catalyst is a molecular sieve with a one-dimensional pore system, such as SM-3, MAPO-11, SAPO-11, SSZ-32, ZSM-23, MAPO-39, SAPO-39, ZSM-22 or SSZ-20. Other possible acidic solid catalysts useful for isomerization include ZSM-35, SUZ-4, NU-23, NU-87 and natural or synthetic ferrierites. These molecular sieves are well known in the art and are discussed in Rosemarie Szostak's Handbook of Molecular Sieves (New York, Van Nostrand Reinhold, 1992) which is herein incorporated by reference for all purposes. A liquid type of isomerization catalyst that can be used is iron pentacarbonyl (Fe$(CO)_5$).

The process for isomerization of normal alpha olefins may be carried out in batch or continuous mode. The process temperatures may range from about 50° C. to about 250° C. In the batch mode, a typical method used is a stirred autoclave or glass flask, which may be heated to the desired reaction temperature. A continuous process is most efficiently carried out in a fixed bed process. Space rates in a fixed bed process can range from 0.1 to 10 or more weight hourly space velocity.

In a fixed bed process, the isomerization catalyst is charged to the reactor and activated or dried at a temperature of at least 150° C. under vacuum or flowing inert, dry gas. After activation, the temperature of the isomerization catalyst is adjusted to the desired reaction temperature and a flow of the olefin is introduced into the reactor. The reactor effluent containing the partially-branched, isomerized olefins is collected. The resulting partially-branched, isomerized olefins contain a different olefin distribution (i.e., alpha olefin, beta olefin; internal olefin, tri-substituted olefin, and vinylidene olefin) and branching content that the unisomerized olefin and conditions are selected in order to obtain the desired olefin distribution and the degree of branching.

Acid Catalyst

Typically, the alkylated aromatic compound may be prepared using acid catalysts (Bronsted or Lewis acids).

Preferably, the acid catalyst is selected from the group consisting of aluminum trichloride, aluminum tribromide, hydrochloric acid, hydrofluoric acid, hydrobromic acid, sulfuric acid, perchloric acid, trifluoromethanesulfonic acid, fluorosulfonic acid, and nitric acid. More preferred, the acid catalyst is aluminum trichloride.

The alkylation process may be carried out in a batch or continuous process. The acid catalyst may be recycled when used in a continuous process. The acid catalyst may be recycled or regenerated when used in a batch process or a continuous process.

The acid catalyst may be regenerated after it becomes deactivated (i.e., the catalyst has lost all or some portion of its catalytic activity). Methods that are well known in the art may be used to regenerate the deactivated acid catalyst.

Process for Preparing Alkylated Aromatic Compound

In one embodiment of the present invention, the alkylation process is carried out by reacting a meta-xylene compound with an olefin or a mixture of olefin compounds in the presence of an acid catalyst, such as aluminum trichloride, in a reactor in which agitation is maintained, thereby producing an alkylated meta-xylene product. An excess amount of meta-xylene may be employed in the alkylation reaction. The acid catalyst may be recycled to the reactor(s) in a closed loop cycle. The hydrocarbon product is further treated to remove excess un-reacted aromatic compounds and, optionally, olefinic compounds from the desired alkylate product. The excess aromatic compounds may also be recycled to the reactor(s).

The total charge mole ratio of the acid catalyst to the mixture of olefin compounds is about 1.0 to 1.

The total charge mole ratio of the meta-xylene compound to the mixture of olefin compounds is about 5.0 to 1.

Many types of reactor configurations may be used. These include, but are not limited to, batch and continuous stirred tank reactors, reactor riser configurations, ebulating bed reactors, and other reactor configurations that are well known in the art. Many such reactors are known to those skilled in the art and are suitable for the alkylation reaction. Agitation is critical for the alkylation reaction and can be provided by rotating impellers, with or without baffles, static mixers, kinetic mixing in risers or any other agitation devices that are well known in the art.

The alkylation process may be carried out at temperatures from about 15° C. to about 65° C. The process is carried out under sufficient pressure that a substantial portion of the feed components remain in the liquid phase. Typically, a pressure of 0 to 150 psig is satisfactory to maintain feed and products in the liquid phase.

The residence time in the reactor is a time that is sufficient to convert a substantial portion of the olefin to alkylate product. The time required is from about 30 seconds to about 120 minutes. A more precise residence time may be determined by those skilled in the art using batch stirred tank reactors to measure the kinetics of the alkylation process.

The meta-xylene compound and the olefin or mixture of olefins may be injected separately into the reaction zone or may be mixed prior to injection. Both single and multiple reaction zones may be used with the injection of the aromatic compounds and the mixture of olefins into one, several, or all reaction zones. The reaction zones need not be maintained at the same process conditions.

The hydrocarbon feed for the alkylation process may comprise a meta-xylene compound and a mixture olefins in which the molar ratio of meta-xylene compound to olefins is from about 0.5:1 to about 50:1 or more. In the case where the molar ratio of meta-xylene compound to olefin is >1.0 to 1, there is an excess amount of aromatic compounds present. Preferably an excess of meta-xylene compounds is used to increase reaction rate and improve product selectivity. When excess meta xylene is used, the excess un-reacted meta-xylene in the reactor effluent can be separated, e.g. by distillation, and recycled to the reactor.

Tri-Alkylsubstituted Alkylated Aromatic Compound

An intermediate product of the presently claimed invention is a tri-alkylsubstituted aromatic compound. Preferably, the resulting intermediate product comprises at least about 60 weight percent of a 1-alkyl-3,5 dimethylsubstituted aromatic compound and no more than 40 weight percent of a 1-alkyl-2,4 dimethylsubstituted aromatic compound. More preferred, the resulting intermediate product comprises at least about 65 weight percent of a 1-alkyl-3,5 dimethylsubstituted aromatic compound and no more than 35 weight percent of a 1-alkyl-2,4 dimethylsubstituted aromatic compound. Even more preferred, the resulting intermediate product comprises at least about 70 weight percent of a 1-alkyl-3,5 dimethylsubstituted aromatic compound and no more than 30 weight percent of a 1-alkyl-2,4 dimethylsubstituted aromatic compound. Most preferred, the resulting intermediate product comprises at least about 75 weight percent of a 1-alkyl-3,5 dimethylsubstituted aromatic compound and no more than 25 weight percent of a 1-alkyl-2,4 dimethylsubstituted aromatic compound. Even most preferred, the resulting intermediate product comprises at least about 80 weight percent of a 1-alkyl-3,5 dimethylsubstituted aromatic compound and no more than 20 weight percent of a 1-alkyl-2,4 dimethylsubstituted aromatic compound. Especially preferred, the resulting intermediate product comprises at least about 85 weight percent of a 1-alkyl-3,5 dimethylsubstituted aromatic compound and no more than 15 weight percent of a 1-alkyl-2,4 dimethylsubstituted aromatic compound. Even especially preferred, the resulting intermediate product comprises at least about 90 weight percent of a 1-alkyl-3,5 dimethylsubstituted aromatic compound and no more than 10 weight percent of a 1-alkyl-2,4 dimethylsubstituted aromatic compound.

Preparation of Alkylated Aromatic Sulfonate

In one embodiment of the present invention, the product prepared by the process described herein (i.e., alkylated aromatic compound: 1-alkyl-3,5 dimethylsubstituted aromatic compound; 1-alkyl-2,4-dimethylsubstituted aromatic compound and mixtures thereof) is further reacted to form a sulfonate.

Sulfonation

Sulfonation of the alkylated aromatic compound may then be performed by any method known to one of ordinary skill in the art. The sulfonation reaction is typically carried out in a continuous falling film tubular reactor maintained at about 55° C. The alkylaryl compound is placed in the reactor along with the sulfur trioxide diluted with air, sulfuric acid, chlorosulfonic acid or sulfamic acid, thereby producing alkylaryl sulfonic acid. Preferably, the alkylylated aromatic compound is sulfonated with sulfur trioxide diluted with air, thereby producing an alkylaryl sulfonic acid compound. The charge mole ratio of sulfur trioxide to alkylate is maintained at about 0.8 to 1.1:1.

Neutralization of Alkylaryl Sulfonic Acid

Neutralization of the alkylaryl sulfonic acid may be carried out in a continuous or batch process by any method known to a person skilled in the art to produce alkylaryl sulfonates. Typically, an alkylaryl sulfonic acid is neutralized with a source of alkali or alkaline earth metal or ammonia. Preferably, the source is an alkali or alkaline earth metal; more preferably, the source is an alkaline earth metal hydroxide, such as but not limited to, calcium hydroxide or magnesium hydroxide.

Other embodiments will be obvious to those skilled in the art.

The following examples are presented to illustrate specific embodiments of this invention and are not to be construed in any way as limiting the scope of the invention.

EXAMPLES

Example 1

Preparation of Alkylxylene Using Aluminum Trichloride Alkylation Catalyst

Example 1A

Alkyation of meta-Xylene with $C_{12}$-$C_{18}$ Normal Alpha Olefin

Alkylxylene was prepared using aluminum trichloride alkylation catalyst. meta-Xylene was alkylated with a $C_{12}$-$C_{18}$ normal alpha olefin in a batch process bench scale unit. Into a 3 liter glass reactor were charged, under nitrogen, 1120.4 grams of meta-xylene and while stirring 18.0 grams of aluminum trichloride was added to the reaction mixture. Next, 443.7 grams of $C_{12}$-$C_{18}$ normal alpha olefin was added to the reactor over 1.5 hours in order to control the temperature increase due to the exothermic reaction. The temperature of the reaction never exceeded 27° C. At the end of the olefin addition, the reaction mixture was maintained at about 26° C. for one hour. After this period, the reaction was quenched with cold distilled water, 50 weight percent solution of sodium hydroxide, and three consecutive water washes to remove the acid catalyst from the organic phase. The organic phase containing the alkylxylene product was dried over magnesium sulfate and the excess meta-xylene was distilled under pressure using a Rotovap evaporator to recover the alkylxylene product.

See Table I for a summary of the analytical data determined by GC and NMR for Example 1A.

Example 1B

Alkyation of meta-Xylene with $C_{12}$-$C_{18}$ Normal Alpha Olefin

Alkylxylene was prepared using aluminum trichloride alkylation catalyst. meta-Xylene was alkylated with a $C_{12}$-$C_{18}$ normal alpha olefin in a batch process bench scale unit. Into a 3 liter glass reactor were charged, under nitrogen, 1120.7 grams of meta-xylene and while stirring 17.8 grams of aluminum trichloride was added to the reaction mixture. Next, 444.0 grams of $C_{12}$-$C_{18}$ normal alpha olefin was added to the reactor over 1.0 hours in order to control the temperature increase due to the exothermic reaction. The temperature of the reaction never exceeded 60° C. At the end of the olefin addition, the reaction mixture was maintained at about 60° C. for one hour. After this period, the reaction was quenched and the alkylxylene recovered as described in Example 1A.

See Table I for a summary of the analytical data for Example 1B.

Example 1C

Alkyation of meta-Xylene with $C_{12}$-$C_{14}$ Normal Alpha Olefin

Alkylxylene was prepared using aluminum trichloride alkylation catalyst. meta-Xylene was alkylated with a $C_{12}$-$C_{14}$ normal alpha olefin in a batch process bench scale unit. Into a 3 liter glass reactor were charged, under nitrogen, 1120.0 grams of meta-xylene and while stirring 15.4 grams of aluminum trichloride was added to the reaction mixture. Next, 384.0 grams of $C_{12}$-$C_{14}$ normal alpha olefin was added to the reactor over 0.5 hours in order to control the temperature increase due to the exothermic reaction. The temperature of the reaction never exceeded 25° C. At the end of the olefin addition, the reaction mixture was maintained at about 24° C. for one hour. After this period, the reaction was quenched and the alkylxylene recovered as described in Example 1A.

See Table I for a summary of the analytical data for Example 1C.

Example 1D

Alkyation of meta-Xylene with $C_{12}$-$C_{14}$ Normal Alpha Olefin

Alkylxylene was prepared using aluminum trichloride alkylation catalyst. meta-Xylene was alkylated with a $C_{12}$-

$C_{14}$ normal alpha olefin in a batch process bench scale unit. Into a 3 liter glass reactor were charged, under nitrogen, 1120.0 grams of meta-xylene and while stirring 15.4 grams of aluminum trichloride was added to the reaction mixture. Next, 384.0 grams of $C_{12}$-$C_{14}$ normal alpha olefin was added to the reactor over 0.5 hours in order to control the temperature increase due to the exothermic reaction. The temperature of the reaction never exceeded 60° C. At the end of the olefin addition, the reaction mixture was maintained at about 60° C. for one hour. After this period, the reaction was quenched and the alkylxylene recovered as described in Example 1A.

See Table I for a summary of the analytical data for Example 1D.

Example 1E

Alkyation of meta-Xylene with $C_{16}$-$C_{18}$ Normal Alpha Olefin

Alkylxylene was prepared using aluminum trichloride alkylation catalyst. meta-Xylene was alkylated with a $C_{16}$-$C_{18}$ normal alpha olefin in a batch process bench scale unit. Into a 3 liter glass reactor were charged, under nitrogen, 1120.1 grams of meta-xylene and while stirring 20.1 grams of aluminum trichloride was added to the reaction mixture. Next, 502.2 grams of $C_{16}$-$C_{18}$ normal alpha olefin was added to the reactor over 0.5 hours in order to control the temperature increase due to the exothermic reaction. The temperature of the reaction never exceeded 60° C. At the end of the olefin addition, the reaction mixture was maintained at about 60° C. for one hour. After this period, the reaction was quenched and the alkylxylene recovered as described in Example 1A.

See Table I for a summary of the analytical data for Example 1E.

TABLE I

| Example | Alkyl Chain Attachment Position | | | Aromatic isomer distribution | |
|---|---|---|---|---|---|
| | 2-attachment | 3-attachment | 4+-attachment | wt % 1-alkyl-3,5-dimethyl-benzene | wt % 1-alkyl-2,4-dimethyl-benzene |
| Example 1A | 58.7% | 18.6% | 22.7% | 71.8% | 28.2% |
| Example 1B | 40.7% | 17.7% | 41.6% | 93.8% | 6.2% |
| Example 1C | 60.3% | 18.9% | 20.8% | 65.8% | 34.2% |
| Example 1D | 39.1% | 18.7% | 42.2% | 94.0% | 6.0% |
| Example 1E | 32.7% | 15.7% | 51.6% | 93.7% | 6.3% |

Example 2

Preparation of Alkylxylene Sulfonic Acids

Alkylxylene sulfonic acids were prepared using the alkylxylenes prepared in Example 1 above. Sulfonation of the alkylxylene was performed in a continuous falling film flow reactor by contacting the alkyl xylene with a stream of air and sulfur trioxide. The molar ratio of the alkylxylene to sulfur trioxide was about 1.0:1.0. The reactor jacket temperature was maintained at around 55° C. The sulfonic acid product was titrated potentiometrically with a standardized cyclohexyamine solution to determine the weight percent of the sulfonic acid and the sulfuric acid in the samples. The results are summarized below in Table II.

TABLE II

| Example | Sulfonic Acid (wt %) | Sulfuric Acid (wt %) |
|---|---|---|
| Example 1A | 90.1 | 1.3 |
| Example 1B | 90.0 | 1.0 |
| Example 1C | 83.2 | 1.6 |
| Example 1D | 83.0 | 1.9 |
| Example 1E | 88.6 | 1.5 |

Example 3

Preparation of Alkylxylene Sulfonates

The alkylxylene sulfonates were prepared using the alkylxylene sulfonic acids prepared in Example 2 above. Neutralization of the sulfonic acid was performed in a beaker with magnetic stirring. The sulfonic acid was heated to about 40° C. to lower the viscosity of the sulfonic acid. Next, a 50 weight percent solution of sodium hydroxide was slowly added to the reaction mixture. The temperature of the reaction was maintained below 80° C. to control the evaporation of water. The sodium hydroxide added was calculated based on sulfonic and sulfuric acid content of each sample (see Example 2). An exact quantity of sodium hydroxide was employed to obtain exactly 100 percent neutralization of the alkylxylene sulfonic acids. The sodium alkylxylene sulfonate was titrated with a standardized hyamine solution to determine the weight percent of the sulfonate in the samples. The results are summarized below in Table IV.

TABLE IV

| Example | Sulfonate (wt %) |
|---|---|
| Example 1A | 79.1 |
| Example 1B | 78.8 |
| Example 1C | 76.9 |
| Example 1D | 77.0 |
| Example 1E | 72.5 |

Example 4

Determination of Enhanced Oil Recovery Performance by Phase Behavior

The sulfonates of Examples 1A, 1B, and 1D were run in phase behavior as outlined by "Experimental Study of the Benefits of Sodium Carbonate on Surfactants for Enhanced Oil Recovery."

[1] Jackson, A. C. "Experimental Study of the Benefits of Sodium Carbonate on Surfactants for Enhanced Oil Recovery." MSE Thesis, University of Texas at Austin, December 2006.

The results for phase behavior are summarized in Table V. The surfactants of the present invention have favorable solubilization ratios that could be useful in a reservoir for enhanced oil recovery. It is desirable to have a solubilization ratio of at least 8. The solubilization ratio is defined as $V_o/V_s$, wherein $V_o$ is the volume of oil solubilized by a unit of volume of petroleum sulfonate reactant, $V_s$, in a middle phase microemulsion at "midpoint" or "optimal salinity". In essence, the solubilization ratio is the measure of how much oil the surfactant can solubilize in an emulsion. The greater the solubilization ratio, the more oil a surfactant can solubilize.

TABLE V

| Example | Solubilization Ratio (cc/cc) | Optimal Salinity (wt % Carbonate) | Equilibration time* |
| --- | --- | --- | --- |
| Example 1A | 24 | 2.1 | <1 week |
| Example 1B | 24 | 2.0 | >1 week |
| Example 1D | 11 | 0.38 | >1 week |

*Equilibration time is defined as how long it takes for the microemulsion that result from the surfactant/oil phase behavior to reach steady state. It is desirable to have an equilibration time of less than 1 week.

What is claimed is:

1. A process for preparing an alkylaryl sulfonate comprising
   (a) reacting at least one meta-xylene compound with an olefin or a mixture of olefins having from about 10 to about 20 carbon atoms, in the presence of an acid catalyst, wherein the resulting product comprises no more than 40 weight percent of 1-alkyl-2,4 dimethyl substituted aromatic compound and at least about 60 weight percent of 1-alkyl-3,5 dimethyl substituted aromatic compound;
   (b) sulfonating the product of (a); and
   (c) neutralizing the product of (b) with a source of an alkali or alkaline earth metal or ammonia.

2. The process according to claim 1 wherein the mixture of olefins is a mixture of branched olefins.

3. The process according to claim 2 wherein the mixture of branched olefins comprises polyolefin compounds derived from $C_3$ or higher monoolefins.

4. The process according to claim 3 wherein the polyolefin compound is either polypropylene or polybutylene.

5. The process according to claim 4 wherein the polyolefin compound is polypropylene.

6. The process according to claim 4 wherein the polyolefin compound is polybutylene.

7. The process according to claim 1 wherein the olefin or the mixture of olefins in step (a) is a mixture of linear olefins, a mixture of isomerized linear olefins, a mixture of branched olefins, a mixture of partially branched olefins, or a mixture thereof.

8. The process according to claim 7 wherein the olefin or the mixture of olefins in step (a) is a mixture of linear olefins.

9. The process according to claim 8 wherein the mixture of linear olefins is a mixture of normal alpha olefins.

10. The process according to claim 9 wherein the mixture of linear olefins comprises olefins derived through cracking of petroleum wax or Fischer Tropsch wax.

11. The process according to claim 8 wherein the mixture of linear olefins is a mixture of linear internal olefins which have been derived from olefin metathesis.

12. The process according to claim 7 wherein the olefin or the mixture of olefins is selected from olefins containing from about 12 carbon atoms to about 18 carbon atoms.

13. The process according to claim 7 wherein the olefin or the mixture of olefins is a mixture of olefins derived from linear alpha olefins or isomerized linear olefins containing from about 12 to about 18 carbon atoms.

14. The process according to claim 1 wherein the acid catalyst is selected from Bronsted or Lewis acids.

15. The process according to claim 14 wherein the acid catalyst is selected from the group consisting of aluminum trichloride, aluminum tribromide, hydrochloric acid, hydrofluoric acid, hydrobromic acid, sulfuric acid, perchloric acid, trifluoromethanesulfonic acid, fluorosulfonic acid, and nitric acid.

16. The process according to claim 1 wherein the resulting product comprises no more than 25 weight percent of 1-alkyl-2,4 dimethylsubstituted aromatic compound and at least about 75 weight percent of 1-alkyl-3,5 dimethyl substituted aromatic compound.

17. The process according to claim 16 wherein the resulting product comprises no more than 10 weight percent of 1-alkyl-2,4 dimethylsubstituted aromatic compound and at least about 90 weight percent of 1-alkyl-3,5 dimethyl substituted aromatic compound.

18. The process according to claim 1 wherein the source of the alkali or alkaline earth metal is a hydroxide.

19. The process according to claim 1 wherein sulfonating the product occurs when the product of (b) is reacted with sulfur trioxide which has been diluted with air.

20. An alkylaryl sulfonate compound prepared by the process according to claim 1.

* * * * *